United States Patent [19]

Cooper

[11] 4,329,994
[45] May 18, 1982

[54] MULTILUMEN CATHETER
[75] Inventor: Robert P. Cooper, Yorba Linda, Calif.
[73] Assignee: American Hospital Supply Corporation, Evanston, Ill.
[21] Appl. No.: 160,749
[22] Filed: Jun. 18, 1980
[51] Int. Cl.$^3$ ............................................ A61M 25/00
[52] U.S. Cl. ................................................ 128/349 B
[58] Field of Search ............... 128/349 B, 672, 673, 128/675, 692, 713, 768; 29/837, 841, 855; 73/204, 301, 362 R, 861.05

[56] References Cited

U.S. PATENT DOCUMENTS

| | | | |
|---|---|---|---|
| 3,038,465 | 6/1962 | Allard et al. ........................ | 128/675 |
| 3,359,974 | 12/1967 | Khalil ................................. | 128/713 |
| 3,448,739 | 6/1969 | Stark et al. ......................... | 128/673 |
| 3,595,079 | 7/1971 | Grahn ................................. | 128/692 |
| 3,710,781 | 1/1973 | Hutchins et al. .................... | 128/675 |
| 3,991,767 | 11/1976 | Miller, Jr. et al. ............... | 128/349 B |
| 3,995,623 | 12/1976 | Blake et al. ........................ | 128/642 |
| 4,024,627 | 5/1977 | Stauffer ............................. | 129/837 |

Primary Examiner—William E. Kamm
Attorney, Agent, or Firm—Tilton, Fallon, Lungmus

[57] ABSTRACT

A multilumen catheter having passages for the flow of gas, the enclosure of electrical leads, and the transmission of fluids for injection and sampling. The gas transmitting lumen also carries the electrical leads which extend to an electrical element disposed within a passage-providing plug located at a point spaced from the catheter's distal end. The plug blocks the entry of fluids into the catheter without at the same time interfering with the flow of gas therethrough. In one embodiment, the passage-providing plug is at least partially preformed and is fitted into the space otherwise occupied by sections of a pair of adjacent lumens, thereby allowing a relatively large electrical element to be mounted within such space; in a second embodiment the element is mounted in a passage-providing plug disposed within a single lumen; and in a third embodiment the element is embedded in a passage-providing plug which is formed in place. Methods for making such catheters are also disclosed.

27 Claims, 15 Drawing Figures

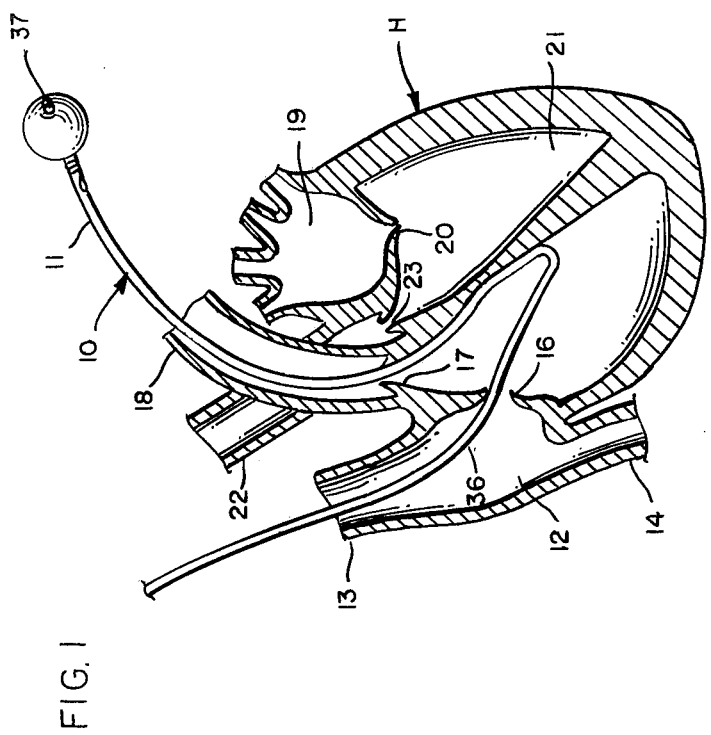
FIG. 1
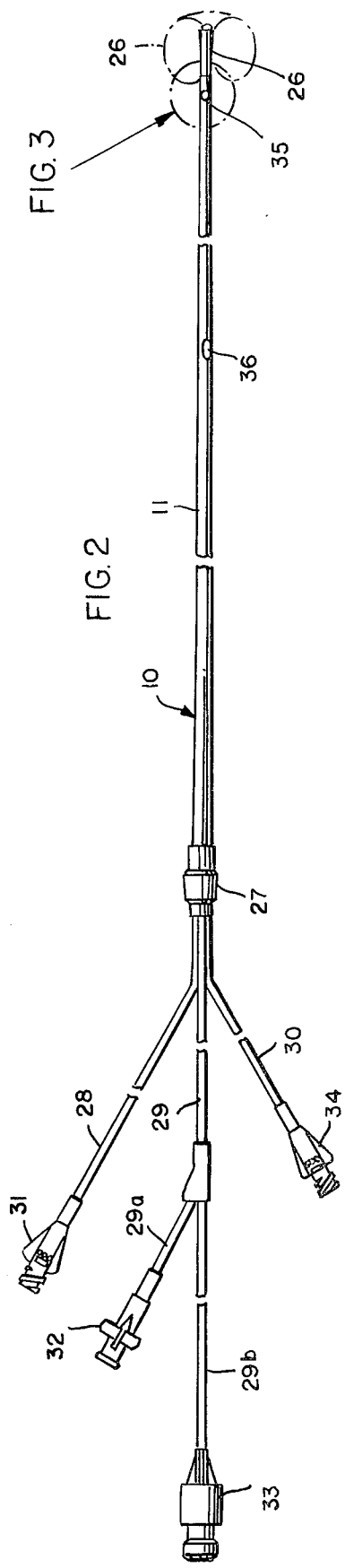
FIG. 2
FIG. 3

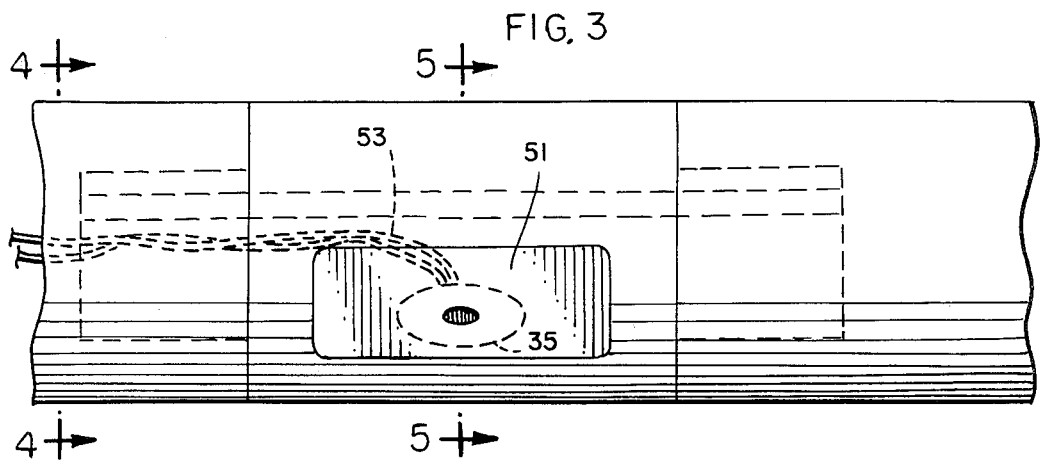
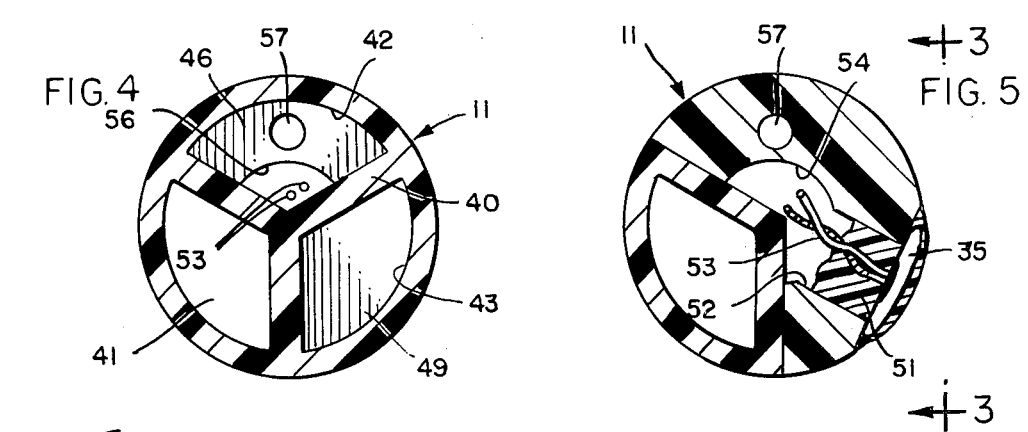
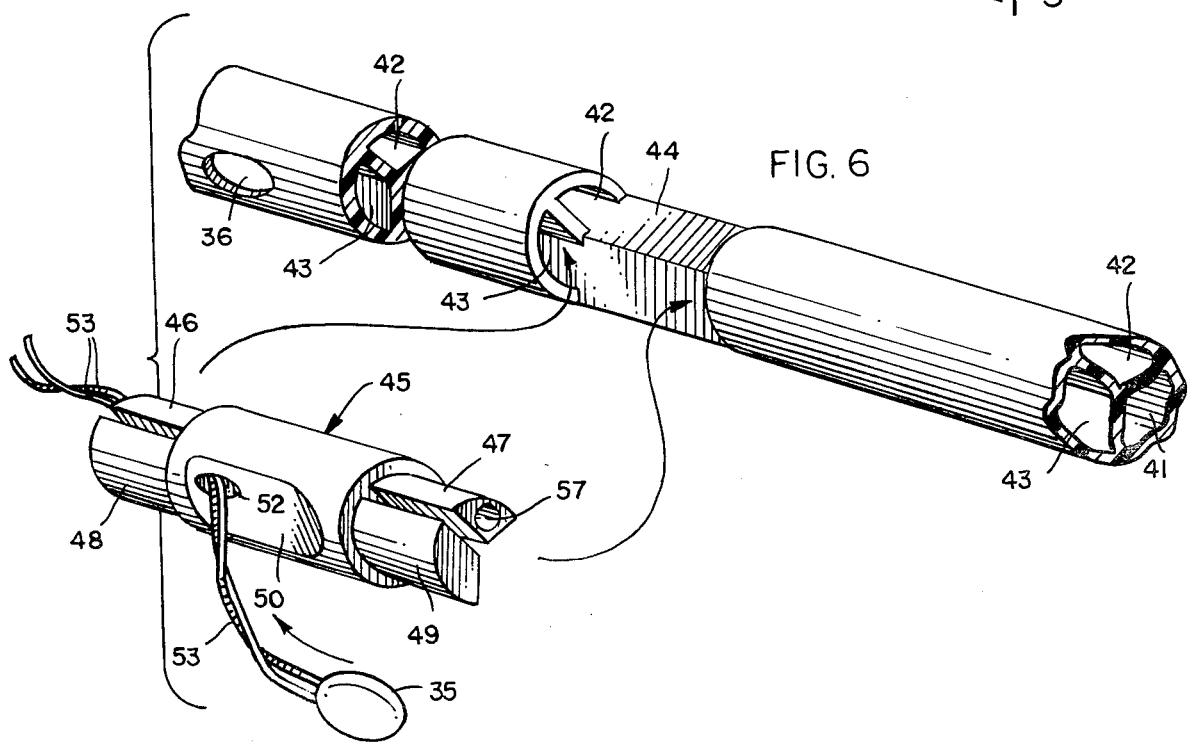

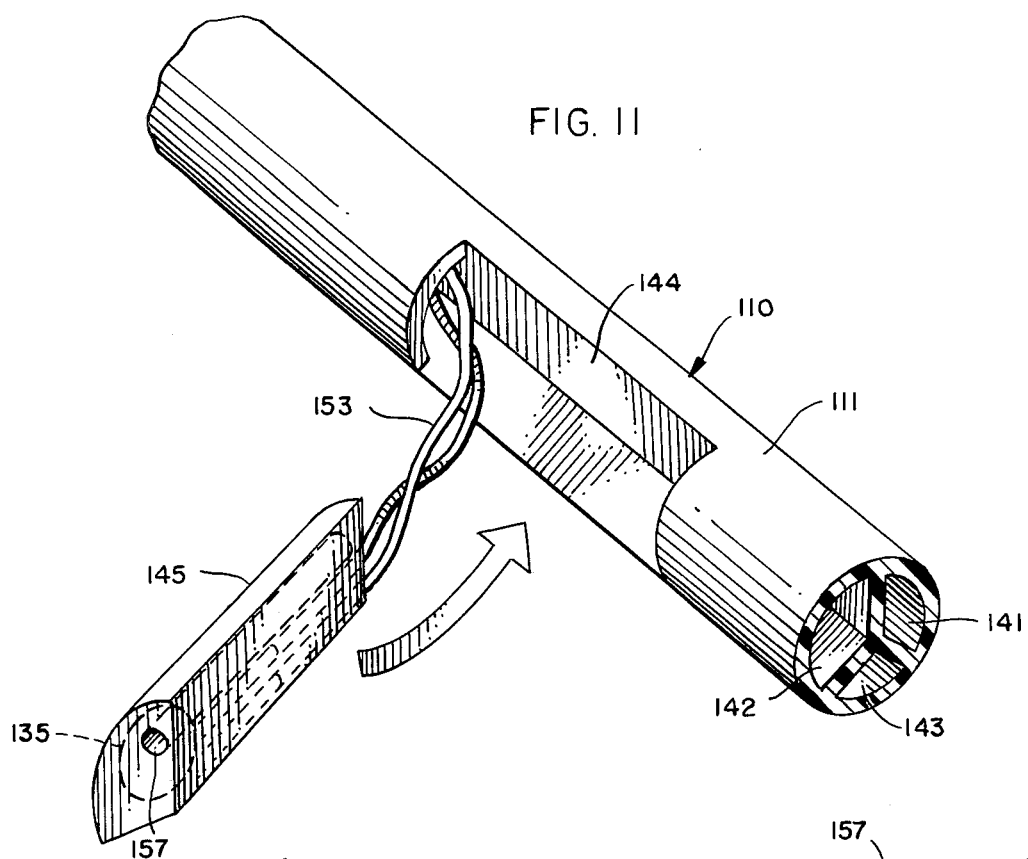
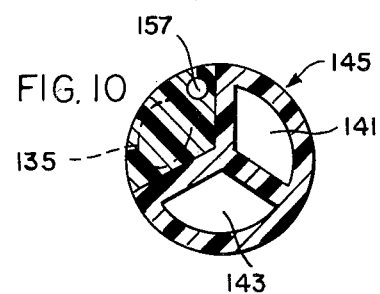
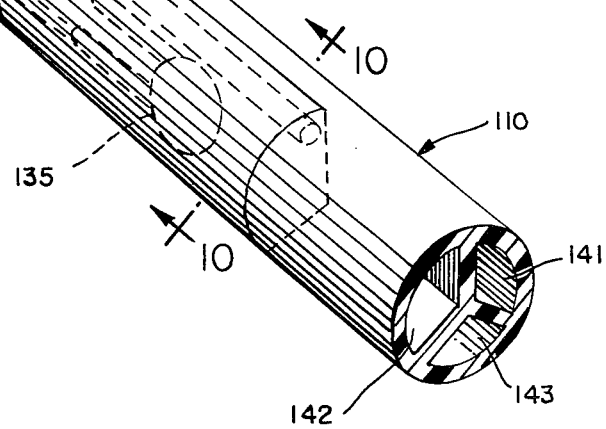

MULTILUMEN CATHETER

BACKGROUND

U.S. Pat. No. 3,995,623 discloses a multilumen flow-directed catheter suitable for use in diagnosing cardiovascular and pulmonary diseases. When the catheter is used for thermodilution measurements, a bolus of cold liquid is injected into the right atrium or superior vena cava (through port 30) and the resultant change in blood temperature is detected by a thermistor (represented by numeral 35) in the pulmonary artery, such change in blood temperature being representative of cardiac output. Three lumens are required by the patented construction to achieve such operation, one lumen conducting gas for balloon inflation, another conveying liquid for the injection of the cold bolus (or for right atrium pressure monitoring, blood sampling, or infusion of therapeutic media) and a third carrying the thermistor leads. One or more additional lumens would be provided where further capabilities are desired; thus, the patent discloses a fourth lumen (C) which extends completely through the cathether body for use in measuring pulmonary arterial pressures when the catheter is in place and the balloon is deflated, or pulmonary capillary wedge pressures when the balloon in inflated.

While the multiple function capability is an important objective, especially for heart catheterization where it is desirable to obtain as much diagnostic information as possible in a single catheterization procedure, such an objective has been achieved in the past either by increasing the size (outside diameter) of such a catheter or by reducing the cross section of each lumen and, hence, lowering the performance characteristics of the catheter. Not only must the lumens be made smaller, if their number is to be increased without altering the catheter's outside dimensions, but the necessity of providing septa between the lumens requires a further reduction in lumen size. Even when the partitions or septa which define the multiple lumens are made as thin as possible, their thickness still substantially reduces the space available for the several lumens within a catheter of any given size. At the same time, the outside dimensions of such a catheter, which must be capable of passing through the vascular system without injury to the patient, must be kept as small as possible. A 4 French catheter (approximately 0.053 inch O.D.) would therefore generally be considered more desirable than a larger 6 French (0.078 inch O.D.) catheter in terms of ease of manipulation and reduced risk of possible complications in use. Consequently, in order to achieve multiple functions in a cardiac catheter of optimum size, it has generally been considered necessary to compromise the performance capabilities of such a catheter.

Other patents disclosing multiple-lumen catheters are U.S. Pat. Nos. 3,746,003, 3,833,004, 3,710,781, 3,634,924, 3,152,592, 3,044,468, 3,050,066, and 2,845,930.

SUMMARY

This invention lies in part in the discovery that the performance characteristics of a multilumen catheter of a given size (O.D.) may be substantially increased by utilizing the gas directing lumen to perform the additional function of housing the electrical leads for an electrical element capable of sensing and/or stimulating physiological activity, and by mounting the electrical element in a plug which defines a passage for the transmission of gas for inflating and deflating a balloon, or for use in the operation of any other pressure responsive means located at or near the distal end of the catheter. The plug is secured within an enlarged recess or cutout formed in the wall of the catheter. In a preferred method of making the catheter, the recess is first formed in the catheter wall, the electrical leads are then threaded through the catheter from the recess to the catheter's proximal end, a suitable electrical element is positioned within the recess and the recess is then plugged so that external flow communication is blocked without at the same time obstructing the flow through the gas transmitting lumen. The plug may be pre-formed or partially pre-formed or, alternatively, may be formed in place. In a preferred form of the invention, the recess communicates with a pair of adjacent lumens to accommodate a relatively large electrical element; when the catheter is completed, the plug occludes one of the lumens and defines a gas flow passage for the other while, at the same time, sealing the recess against external communication. In another form of the invention, the recess extends into only a single lumen, the lumen which transmits gas, and the element-supporting plug received in that recess then seals the lumen against external communication without at the same time preventing the flow of gas therethrough. In all constructions, the lumen used for gas transmission also serves the additional function of housing the electrical leads for the electrical element mounted in the lateral recess of the catheter; hence, a catheter made in accordance with this invention has superior flow capacity and other performance characteristics when compared with a conventional multilumen catheter of similar outside dimensions in which each lumen performs only a single function. Viewed differently, the present invention makes it possible to reduce substantially the outside dimensions of a plural-lumen catheter without at the same time reducing its performance characteristics.

Other objects and advantages of the invention will be apparent from the specification and drawings.

DRAWINGS

FIG. 1 is a somewhat diagrammatic sectional view illustrating a flow-directed catheter embodying this invention when such a catheter is positioned for use.

FIG. 2 is a side elevational view of the catheter.

FIG. 3 is an enlarged broken longitudinal view of that portion of the catheter indicated in FIG. 2.

FIG. 4 is a transverse sectional view taken along line 4—4 of FIG. 3.

FIG. 5 is a transverse sectional view taken along line 5—5 of FIG. 3.

FIG. 6 is an exploded fragmentary perspective view illustrating a catheter prior to insertion of the electrical leads and sealant plug.

FIG. 9 is a fragmentary perspective view of a portion of a multilumen catheter constituting a second embodiment of this invention.

FIG. 10 is a transverse sectional view taken along line 10—10 of FIG. 9.

FIG. 11 is a perspective view illustrating the method of assembly of the catheter of FIG. 9.

DETAILED DESCRIPTION

Figure 7:
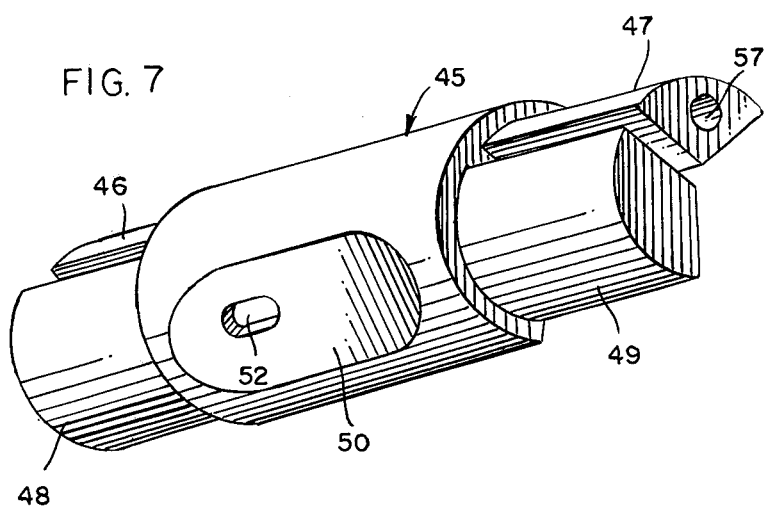
FIG. 7 is an enlarged perspective view of the sealant plug viewed from its outer side.

FIG. 1 illustrates a catheter 10 extending to the right side of a patient's heart H. In brief, the parts of the heart and their operation are as follows: the right atrium 12 receives blood from the superior and inferior vena cava veins 13 and 14 and pumps such blood into the right ventricle 15 through tricuspid valve 16. From the right ventricle, the blood travels to the lungs through pulmonary valve 17 and pulmonary artery 18. Oxygenated blood returning from the lungs enters left atrium 19 and then passes through mitral valve 20 into right ventricle 21. The blood leaves the heart through aorta 22 after passing through aortic valve 23.

Catheter 10 is depicted as a multiple-purpose flow-directed catheter having a tubular body 11 equipped at its distal end with pressure responsive means in the form of a balloon 26. At its proximal end, the catheter body terminates in a coupling 27 which operatively connects the lumens of the catheter to connector tubes 28, 29, and 30. Connector tube 29 bifurcates to provide branches 29a and 29b and, as well known in the art, all of the tubes or branches are provided with coupling elements 31–34 for attaching the connector tubes to syringes or other devices.

The structure as so far described is essentially conventional. In use, the soft, pliable catheter body is introduced into the vascular system from the antecubital, femoral, subclavian, or jugular areas and is advanced, with the balloon in deflated or only partially inflated condition, into the right atrium 12. The balloon is then inflated to its maximum recommended capacity and the flow of blood through the heart rapidly propels the inflated balloon-tipped catheter from the right atrium into the pulmonary artery 18 (FIG. 1). It will be observed that when the catheter is so positioned, balloon 26 has advanced through the pulmonary artery into what is generally referred to as the pulmonary capillary wedge position, a sensor or other electrical element 35 at the distal end portion of the catheter body (just proximal to the balloon 26) is disposed within the pulmonary artery, and a lateral flow port 36, sometimes referred to as a proximal port (in contra distinction to distal port 37 at the tip of the catheter body distal to the balloon) is positioned within right atrium 12. With the catheter so positioned, a variety of diagnostic procedures may take place, all of which are well known and, therefore, will be described only briefly here. Port 36 may be used for taking pressure measurements from the right atrium, for injecting or infusing solutions, or for taking blood samples, whereas distal port 37 may also be used for sampling, infusion or injection, or measuring pulmonary artery and pulmonary capillary wedge pressures (depending on whether such measurements are taken with balloon 26 inflated or deflated). In thermodilution measurements, a sterile, cold solution is injected into the right atrium through port 36 and the resulting change in blood temperature is detected by thermistor 35, thereby allowing calculation of cardiac output.

It is to be understood that the electrical element 35 need not take the form of a thermistor; it may, for example, be an electrode for sensing (or, if necessary, stimulating) electrical activity of the heart as disclosed in detail in co-owned U.S. Pat. No. 3,995,623. However, unlike the construction disclosed in that patent, which has four lumens extending through the catheter body, the catheter of the present invention is capable of performing the same functions with only three lumens.

As shown most clearly in FIG. 4, the catheter body 11 is divided by a three-branched partition or septum 40 so that it defines three parallel lumens 41, 42, and 43. Lumen 41 is a through-lumen which communicates with connector tube 28 and which extends all of the way to distal port 37. Such a lumen is illustrated because of the functions already described with which such distal port is associated; if such functions are regarded as unnecessary, then it is to be understood that through lumen 41 may be eliminated and the space that would otherwise be occupied by that lumen may be used for increasing the size of lumens 42 and 43, or for providing a lumen intended to perform some other purpose, or for reducing the outside cross sectional dimensions of the catheter body.

Lumen 42 is a passage which communicates with connector tube 29 and which conveys gas to and from the distal end of the catheter for operation of the balloon 26. The gas of choice is carbon dioxide because of its relatively rapid diffusion rate in blood should the balloon rupture; however, it is conceivable that other gases might be used or even recommended under special circumstances.

Furthermore, while a balloon is represented in the drawings and described in detail herein for purposes of illustration, other types of pressure responsive means might be substituted. For example, the pressure responsive means might take the form of a diaphragm-equipped pressure transducer for measuring blood pressure at or near the tip of the catheter, the gas transmitting lumen in such as case serving to vent the backside of the diaphragm to atmosphere.

Where the pressure responsive element 26 comprises a balloon as shown, the gas enters and leaves the balloon through a lateral port formed in the wall of the catheter body over which the balloon extends. The balloon 26 may be secured in place in any suitable manner, reference being made to U.S. Pat. Nos. 3,995,623, 3,746,003, and 3,833,004 for further information in that regard. Since balloon-attachment methods and constructions are well known in the art and form no part of the present invention, a more detailed description is believed unnecessary herein. It should be noted, however, that the balloon is shown in its fully deflated condition in solid lines in FIG. 3 and in fully inflated condition by phantom lines in that same figure.

Lumen 43 is the lumen which carries liquids to or from proximal port 36. As indicated, that port is so named because it is a substantial distance from the tip of the catheter and from distal port 37; however, as shown in FIGS. 1 and 2, port 36 is actually located in an intermediate position. Thus, in a typical catheter having a total body length of approximately 110 centimeters, the distance between the proximal port 36 and the distal tip would ordinarily fall within the range of approximately 15 to 35 centimeters, such distance being selected so that when the catheter is positioned as shown in FIG. 1 port 36 will be disposed in the right atrium or superior vena cava.

Catheter body 11 is cut away to define a recess 44 at a point spaced distally from port 36 and just proximal to balloon 26 (FIG. 6). The recess communicates with lumens 42 and 43, but not with through-lumen 41. A pre-formed plug 45 is disposed within the recess and, as shown most clearly in FIG. 6, has insert portions 46 and 47 which are received in those portions of lumen 42 immediately adjacent the recess, and with insert portions 48 and 49 which are similarly received within the portions of lumen 43 adjoining the recess. With the exception of insert portion 46, all such portions are shaped to fit snugly within the lumens in which they are received. Such insert portions, and the plug as a whole, are adhesively secured in place. As a result, lumen 43 is completely occluded by the plug. Liquids drawn into or discharged from proximal port 36 cannot flow distally through lumen 43 beyond plug 45, cannot escape through recess 44, and cannot enter parallel lumens 41 or 42.

The plug 45 is formed with an external depression 50 illustrated most clearly in FIGS. 5, 6 and 7. The depression is dimensioned to accommodate the thermistor or other electrical element 35 so that when the element is adhesively secured within the depression the exposed surface of that element will not project appreciably beyond the adjacent cylindrical surfaces of the plug and catheter body. Ideally, the adhesive sealant which secures the element in place may also serve as an embedding medium which fills any peripheral indentations that might otherwise exist about the margin of the element, as indicated by numeral 51 in FIG. 5. The medium 51 may also extend into opening 52 which communicates with depression 50 and through which the electrical leads or conductors 53 of element 35 extend (FIG. 5). In any event, element 35, which is shown as taking the form of a thermistor, is sealed to plug 45 within depression 50 so that fluids cannot enter or leave through opening 52.

Figure 8:
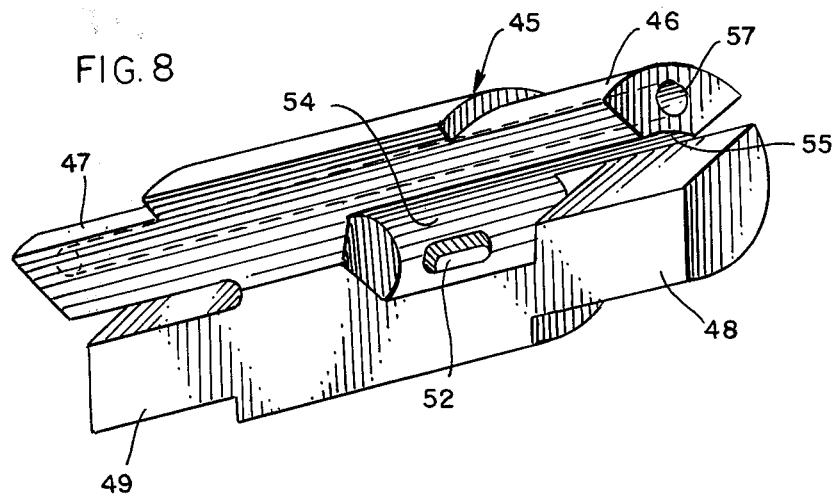
FIG. 8 is a perspective view of the sealant plug viewed from its inner side.

Referring to FIG. 8, it will be observed that opening 52 communicates with a chamber 54 and that the apical or axially disposed edge portion of insert 46 is cut away at 55. When plug 45 is sealed within the recess 44 of the catheter body, with the insert portions 46-49 of the plug sealed to the inner surfaces of lumens 42 and 43, the void created by the removed apical portion of insert 46 defines a passage 56 (FIG. 4) which communicates both with that portion of lumen 42 proximal to plug 45 and with chamber 54 along the inside of the plug. Leads 53 extend from the electrical element 35 through opening 52, chamber 54, and passage 56 into the proximal portion of lumen 42. Such leads continue proximally into connector tube 29, branch 29b, and coupling 33. As is well known, coupling 33 may be connected to a thermodilution cardiac output computer or, should element 35 take the form of an electrode rather than a thermistor, to other appropriate electronic equipment.

When plug 45 is sealed in place within the recess 44 of catheter body 11, the only outlets for chamber 54 are opening 52 and passage 56. Since opening 52 is closed by sealant 51 and electrical element 35, there is no possibility for liquids to enter opening 52, chamber 54, passage 56, or lumen 42 from the area external to plug 45 or from any adjacent lumen. Liquids cannot therefore gain access to leads 53 from either the recessed portion of the catheter in which the plug is received or from other lumens. Additional protection is provided by the fact that the wires or leads 53 are insulated, although such insulation is intended primarily to prevent the conductors from making electrical contact with each other.

Plug 45 also has a longitudinal passage 57 which extends the full length of the plug and is offset from the longitudinal axis of the catheter. As shown most clearly in FIGS. 4-8, passage 57 extends through insert portions 46 and 47 and through the enlarged body portion of the plug therebetween to define a passage for the flow of gas for inflating and deflating balloon 26. Consequently, lumen 42 performs the dual functions of housing the electrical lead for electrical element 35 and defining an uninterrupted passage for the flow of gas through the catheter body. The plug 45 provides for the continuity of that passage while at the same time sealing the proximal and distal portions of lumen 42 against ingress and egress of liquid, occluding lumen 43 at a point distal to port 36, and providing an insulating mounting for electrical element 35.

It is believed apparent that any of a variety of suitable materials may be used for the catheter body, plug, and sealant medium. Polyvinyl chloride has been found to be a particularly effective material for both the catheter body and the plug. The sealant material may be vinyl cyclohexanone, although other well known materials such as epoxy resins or urethane sealants may be used.

In the embodiment illustrated in FIGS. 9-11, the catheter 110 is identical to the catheter already described except for recess 144 and plug 145. Like plug 45, plug 145 is pre-formed; however, it is dimensioned to be received within a relatively small recess 144 which communicates only with lumen 142 and not with through-lumen 141 or lumen 143, the latter of which communicates with a suitable proximal port (not shown) identical to port 36. The plug 145, along with electrical element (thermistor) 135 sealed or embedded therein, and with electrical leads 153 projecting therefrom, may constitute a unitary subassembly which may be inserted into recess 144 during a later stage in the manufacture of the complete catheter as indicated in FIG. 11. Leads 153 would be threaded in a proximal direction from recess 144 and, with the leads fully in place, the pre-formed plug 145 would then be secured in place within the recess by the use of a suitable adhesive or sealant material as already described.

The plug 145 has a longitudinal passage 157 therethrough for the flow of gas to and from the pressure responsive means. Hence, the plug provides a mounting for the electrical element and seals lumen 142 against the inflow of liquid without at the same time preventing the use of lumen 142 for balloon inflation/deflation or other gas transmitting purposes.

Figure 12:
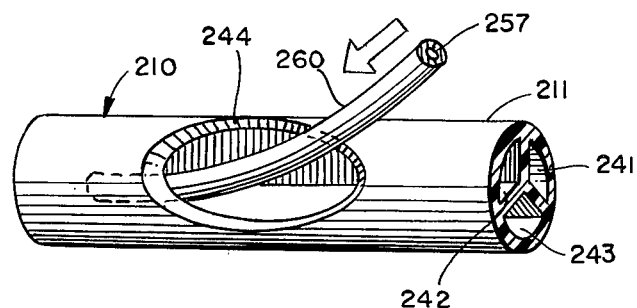
FIGS. 12–15 are fragmentary perspective views illustrating a third embodiment of this invention and the method of making that embodiment.
Figure 13:
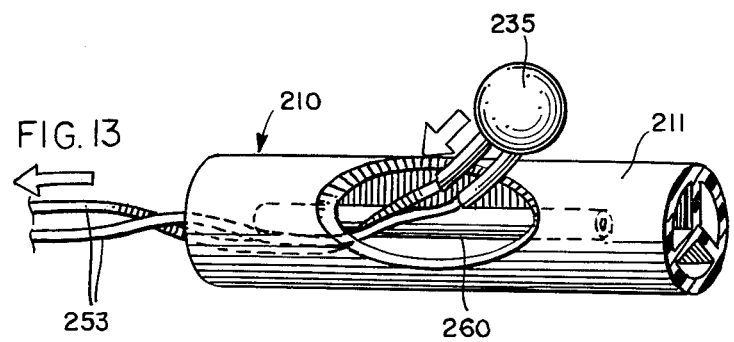
Figure 14:
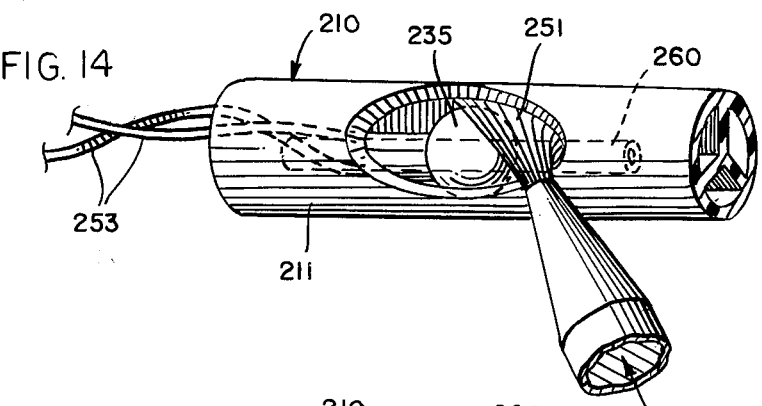
Figure 15:
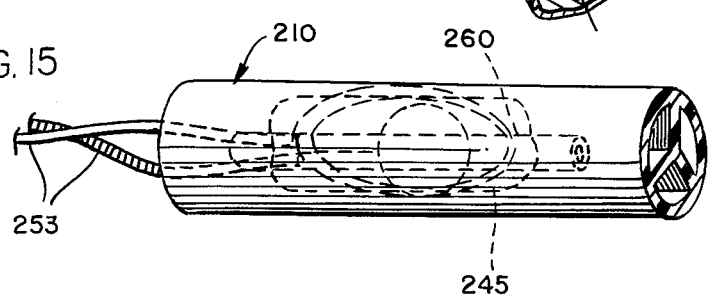

The embodiment of FIGS. 12-15 is similar to the forms already described except that sealant plug 245 is formed in place rather than being wholly or partially pre-formed. Catheter 210 is, except as noted below, identical to catheters 10 and 110. A recess 244 is formed in the wall of catheter body 211, the recess communicating with lumen 242. A flexible tube 260, having a passage 257 therethrough, is inserted into lumen 242 through recess 244 as shown in FIG. 12. Thereafter, the leads 253 of electrical element 235 are fed into lumen 242 through the recess and are urged proximally until they extend beyond the proximal end of the catheter and may be secured to a suitable coupling. A suitable sealant and embedding material 251 is then injected into the recess (FIG. 14) to mount the element 235 and to seal lumen 242 against the ingress of liquids. When the liquid sealant hardens, a plug 245 is formed and, since tube 260 extends beyond the axial limits of that plug, gas may pass freely through the plug to and from the balloon or other pressure responsive element at or near the catheter's distal end.

In the preferred embodiment of FIGS. 3-8, electrical element 35 may be pre-mounted within depression 50, with leads 53 projecting from the plug and available for insertion into lumen 42 through recess 44 or, alternatively, the electrical element may be sealed within the depression at the same time that the plug 45 is adhesively secured within the recess. In other words, plug 45, element 35, and leads 53 may constitute a unitary subassembly, similar to the subassembly described in connection with the embodiment of FIGS. 9–11, or they may be only partially assembled prior to insertion of plug 45 into recess 44.

While in the foregoing several embodiments of this invention have been disclosed in considerable detail for purposes of illustration, it will be understood by those skilled in the art that many of these details may be varied without departing from the spirit and scope of the invention.

I claim:

1. A catheter comprising a catheter body having an elongated tubular wall formed of flexible material and having proximal and distal ends; pressure responsive means mounted upon said body adjacent the distal end thereof; said body having a lumen extending from said proximal end to said distal end and communicating with said pressure responsive means; said body also having a recess in the wall thereof proximal to said means and communicating with said lumen; a plug disposed within said recess and sealed to said body to prevent liquid flow into said lumen through said recess; said plug having a longitudinal passage for the flow of gas therethrough; and an electrical element sealed in said plug and having electrical conducting means associated therewith and extending from said plug through the portion of said lumen proximal to said plug.

2. The catheter of claim 1 in which said electrical element is a thermistor.

3. The catheter of claim 1 in which said plug is preformed of resilient material and is adhesively sealed to said catheter body within said recess.

4. The catheter of claim 1 in which said body includes a second lumen extending parallel to said first lumen and separated therefrom by a longitudinal septum.

5. The catheter of claim 4 in which said second lumen is a through-lumen having a distal opening beyond said balloon.

6. The catheter of claim 4 in which said catheter body has a proximal port extending through said wall and communicating with said second lumen at a point proximal to said plug.

7. The catheter of claim 6 in which said body includes a third lumen extending parallel to said first and second lumens and separated therefrom by a longitudinal septum; said third lumen being a through-lumen having a distal opening beyond said pressure responsive means.

8. The catheter of claim 6 in which said recess communicates with both of said lumens, and said plug is sealed to said body within said recess to block fluid flow into, out of, and through said second lumen at said recess.

9. The catheter of claim 6 in which said plug includes end portions projecting into and sealed within said first and second lumens.

10. The catheter of claim 1 in which said plug includes reduced end portions projecting into and sealed within said lumen on the distal and proximal sides of said recess.

11. The catheter of claim 1 in which said plug includes a tube disposed longitudinally within said lumen and projecting distally and proximally beyond the remainder of said plug.

12. The catheter of claim 1 in which said pressure responsive means comprises a balloon.

13. A multilumen catheter comprising a catheter body having an elongated tubular wall formed of flexible material and having proximal and distal ends; pressure responsive means mounted upon said body adjacent the distal end thereof; said body having a first lumen extending from said proximal to said distal end and communicating with said pressure responsive means; said body also having a second lumen for conducting liquids through said catheter, said second lumen being separated from said first lumen by a longitudinal septum; a recess in the wall of said body proximal to said balloon and communicating with both said first and second lumens; a plug disposed within said recess and sealed to said catheter body to prevent the entry and exit of fluids through said recess and to provide a seal to block the flow of liquid in a distal direction through said second lumen, said plug having a longitudinal passage therethrough communicating only with said first lumen for the flow of gas therethrough; and an electrical element sealed to said plug and including electrical conducting means extending through the portion of said first lumen proximal to said plug.

14. The catheter of claim 13 in which said electrical element is a thermistor.

15. The catheter of claim 13 in which said plug is pre-formed of resilient material and is adhesively secured to said catheter body within said recess.

16. The catheter of claim 15 in which said body includes a third lumen parallel to said first and second lumens and separated therefrom by said longitudinal septum, said third lumen being a through-lumen having a distal opening beyond said pressure responsive means.

17. The catheter of claim 13 in which said body has a proximal port extending through said wall and communicating with said second lumen at a point proximal to said plug.

18. The catheter of claim 13 in which said pressure responsive means comprises a balloon.

19. The catheter of claim 13 in which said plug includes end portions projecting into and sealed within said first and second lumens.

20. A method of mounting an electrical element in a catheter having a gas transmitting lumen, comprising the steps of forming a recess through the wall of said catheter intermediate the distal and proximal ends thereof, said recess communicating with said lumen; inserting at least one electrical lead into said lumen to locate the same between said recess and the catheter's proximal end; and positioning and sealing an electrical element within said recess to block the flow of fluids into and out of said catheter through said recess without at the same time preventing the flow of gas through said lumen.

21. The method of claim 20 in which said positioning and sealing steps include first inserting a tube through said recess into said lumen, then locating said electrical element within said recess, and then injecting a sealant into said recess to fix said electrical element and tube in place.

22. The method of claim 20 in which said positioning and sealing steps include inserting a preformed plug into said lumen through said recess, said plug having a longitudinal passage for the flow of gas therethrough, and then sealing said plug and electrical element in place.

23. The method of claim 22 in which said electrical element is secured to said pre-formed plug prior to insertion of said plug into said lumen.

24. The method of claim 20 in which said catheter has a second lumen and said recess is formed to communicate with both said first-mentioned and said second lumens; said positioning and sealing steps including the steps of sealing said second lumen to prevent the flow of fluids into and out of said second lumen at said recess.

25. The method of claim 24 in which said preformed plug has end portions receivable in said first and second lumens; said positioning and sealing steps including positioning and sealing said end portions within said lumens on the distal and proximal sides of said recess.

26. The method of claim 20 in which said electrical lead is inserted into said lumen through said recess and is urged in a proximal direction therefrom.

27. The method of claim 26 in which said electrical lead is secured at its distal end to said electrical element prior to insertion of said lead into said lumen through said recess.

* * * * *